United States Patent [19]
Gopalkrishnan et al.

[11] Patent Number: 5,919,830
[45] Date of Patent: Jul. 6, 1999

[54] STABLE NON-AQUEOUS BLENDS FOR PERSONAL CARE COMPOSITIONS

[76] Inventors: Sridhar Gopalkrishnan, 8641 Woodside Dr., Grosselle, Mich. 48136; Richard J. Holland, 19 Pleasant Ct., Flanders, N.J. 07836; Kathleen M. Guiney, 423 Maple St., Wyandotte, Mich. 48192

[21] Appl. No.: 09/070,386

[22] Filed: Apr. 30, 1998

[51] Int. Cl.$^6$ ............... A61K 7/00; A61K 7/16; A61K 47/10

[52] U.S. Cl. .......... 514/772.1; 514/901; 514/941; 514/944; 514/950; 514/969; 514/975; 424/401; 424/49; 424/65; 424/69; 424/70.31; 424/76.1; 424/78.3; 424/78.38

[58] Field of Search .............. 424/401, 49, 65, 424/69, 70.31, 76.1, 78.3, 78.38; 514/772.1, 901, 941, 944, 950, 969, 975

[56] References Cited

U.S. PATENT DOCUMENTS

| | | |
|---|---|---|
| 3,740,421 | 6/1973 | Schmolka . |
| 3,867,533 | 2/1975 | Schmolka . |
| 3,997,458 | 12/1976 | Kurtz . |
| 4,382,078 | 5/1983 | Berkoff et al. . |
| 4,465,663 | 8/1984 | Schmolka . |
| 4,476,107 | 10/1984 | Schmolka . |
| 5,035,880 | 7/1991 | Mori et al. . |
| 5,057,307 | 10/1991 | Hill et al. . |
| 5,073,368 | 12/1991 | Subramanian . |
| 5,096,698 | 3/1992 | Mitchell et al. . |
| 5,256,396 | 10/1993 | Piechota . |
| 5,374,368 | 12/1994 | Hauschild . |
| 5,709,852 | 1/1998 | Gopalkrishnan et al. . |

FOREIGN PATENT DOCUMENTS

| | | |
|---|---|---|
| 0 546 627 A1 | 6/1993 | European Pat. Off. . |
| 0-551-626 | 7/1993 | European Pat. Off. . |
| WO 93/13750 | 7/1993 | European Pat. Off. . |
| WO 95/01155 | 1/1995 | European Pat. Off. . |

*Primary Examiner*—Frederick Krass
*Attorney, Agent, or Firm*—Joanne P. Will

[57] ABSTRACT

A stable non-aqueous carrier for personal care compositions comprising:
   a) about 80–98% by weight of a liquid polyoxyalkylene glycol of MW=3000–100000;
   b) about 2–20% by weight of a non-ionic solid triblock EO/PO/EO copolymer of MW=8500–25,000.

4 Claims, No Drawings

STABLE NON-AQUEOUS BLENDS FOR PERSONAL CARE COMPOSITIONS

FIELD OF THE INVENTION

The present invention relates to stable, non-aqueous blends comprising a liquid polyoxyalkylene compound and a solid ethylene oxide/propylene oxide/ethylene oxide (EO/PO/EO) triblock copolymer useful as carriers for personal care products wherein said carrier comprises approximately 15–5% of said personal care product.

BACKGROUND

Non aqueous personal care compositions can typically contain major amounts of a non-aqueous carrier which provides a suitable matrix into which the active ingredients, such as personal care actives or pharmaceutical actives, and other functional ingredients, are added to form personal care products that are usually pasty in appearance. It is known in the art that the non-aqueous carrier can be composed of a blend of liquid component(s) and solid component(s) to provide a stable suspension during the formulation of said personal care compositions. For example, the typical liquid components in a essentially non-aqueous personal care composition are polyethylene glycol polymers of low molecular weight, typically in the range of 200–400. The solid component which is usually added to modify the rheology of the composition can be a higher molecular weight polyethylene glycol of molecular weights between 1,000–10,000. Such mixtures of a liquid polyethylene glycol and a solid polyethylene glycol have the consistency of an ointment. In addition, liquid polyethylene glycols are excellent solvents for a variety of flavor oils and pharmaceutical actives. Furthermore, such blends allow the flexibility of formulating actives and other functional ingredients that are water-sensitive, in a non-aqueous medium, while at the same time, possess good solubility in water. These blends are therefore suitable as bases for ointment formulations. For purposes of designing a suitable non-aqueous medium with liquid polyethylene glycols, liquid polyethylene glycols are combined with another additives of a specific molecular weight, in a select ratio to achieve the appropriate consistency. The choice of the additive is limited to solid polyethylene glycols of molecular weights typically ranging from about 1000 to about 10000. The function of the solid polyethylene glycol is limited to providing adequate rheology or the desired consistency to the composition. Many personal care compositions can contain additional functional ingredients that provide specific benefits to a composition such as foam boosting, defoaming, emulsification, detergency, suspending, wetting, dispersing, irritation mitigation, solubilizing, and lubrication. Examples of such ingredients are the nonionic triblock copolymers of ethylene oxide and propylene oxide which are available in a wide range of molecular weights and in various proportions of ethylene oxide and propylene oxide. Applicants have observed that in the design of a non-aqueous medium such as the one stated above, if the solid polyethylene glycol were to be replaced with a solid nonionic triblock surfactant comprising ethylene oxide and propylene oxide, the resulting non-aqueous blend is not very stable above moderately ambient temperatures. These blends tend to liquefy and lose a substantial portion of their viscosity at moderately ambient temperatures or split in to two phases at ambient temperatures. Personal care compositions or pharmaceutical compositions comprising such a carrier are subject to separation of the active ingredients due to the loss of viscosity or suspending ability of the carrier. This could lead to an overdose or underdose of active ingredients with potentially serious consequences.

Further, personal care products, such as mouthwashes, cosmetic creams, gels and lotions, antiperspirants, deodorants, and over-the-counter medicaments such as salves and ointments, which are formulated comprising a non-aqueous blend, are subject to freeze-thaw cycles during shipment and storage. Subjecting such personal care products to several freeze thaw cycles can alter the rheology of the product, creating a product dispensing problem when the product becomes too hard or too soft or too viscous, and hence, difficult to use. Thus, there is a need for a non-aqueous carrier which offers a wide formulation flexibility and has the ability to withstand the extremes of transportation temperatures without significantly altering the rheology and the integrity of the composition.

The art is replete with non-aqueous carrier blend formulations. Specifically, WO 95/01155, discloses the use of a non-ionic surfactant as a stabilizing agent in antibody containing oral compositions at levels of 0.01–6% by weight of the oral composition. Preferred non-ionic surfactants are the solid EO/PO/EO triblock copolymers known as PLURONIC® F 68, F 88 and F 108. U.S. Pat. No. 5,374,368 describes the use of liquid EO/PO/EO triblock co-polymers (PLURONIC® L 31 and L 35) in stable hydrogen peroxide releasing dental care compositions at levels of 55–90% by weight of the dental care composition. U.S. Pat. No. 3,740,421 discloses gel forming solid EO/PO/EO triblock copolymers useful in cosmetic and personal care formulations at levels of approximately 20–25% by weight. Preferred solid EO/PO/EO triblock copolymers have a molecular weight of 4,600–16,000. Said solid EO/PO/EO triblock copolymers form a gel when added to an aqueous solution. U.S. Pat. No. 3,867,533 discloses aqueous gel compositions containing solid EO/PO/EO triblock copolymers, having a molecular weight of 6,450–20,000 useful at levels of approximately 20% by weight. Said compositions are useful in preparing cosmetic formulations. U.S. Pat. No. 3,997,458 discloses solid triblock co-polymers of EO/PO/EO useful in wound cleansing compositions at levels of approximately 10% by weight. Said EO/PO/EO copolymers have a molecular weight of 5,000–13,500 (e.g., PLURONIC® F 98, F 108 - available from BASF Corporation, Mt. Olive, N.J.). U.S. Pat. No. 4,382,078 discloses water based aerosol compositions containing a dimethylether propellant and solid EO/PO/EO triblock copolymers at levels of 1–6% by weight. U.S. Pat. No. 4,465,663 discloses clear aqueous cosmetic gels containing solid EO/BO(butylene oxide)/EO triblock copolymers at levels of approximately 20%. U.S. Pat. No. 5,035,880 discloses a stable dentrifice compositions containing a cetylpyridinium bactericide and EO/PO/EO solid triblock copolymers (PLURONIC® F 127), and polyethylene glycol at levels of 15–80% by weight. U.S. Pat. No. 4,476,107 discloses a mouthwash containing EO/BO (butylene oxide)/EO triblock copolymers at levels of 0.5–5.0% by weight. U.S. Pat. No. 5,057,307 discloses oral hygiene gels containing non-ionic surfactants, coating substances; and viscosifiers. Said non-ionic surfactants are PLURONIC® F 108 and F 127 available from BASF Corporation, Mt. Olive, N.J. U.S. Pat. No. 5,256,396 discloses a topical composition comprising an EO/PO/EO solid triblock copolymer (PLURONIC® F 127) used at a level of more than 10% to about 17% by weight. EPO-546-627A discloses mouthwash compositions comprising solid EO/PO/EO triblock copolymers such as PLURONIC® 108, 88 at levels of 0.5–3% by weight. EP 0-551-626 discloses a thermoreversible pharmaceutical gel comprising solid EO/PO/EO triblock copolymer such as PLURONIC® F 127 at a level of 10 to 30% by weight. U.S. Pat. No. 5,073,368 discloses mouthwashes containing solid EO/PO/EO triblock copolymers such as PLURONIC® F 87 at levels of 0.1–3% by weight. WO 93113750 discloses an ocular cleansing composition comprising solid PLURONIC® P 85 and paste PLURONIC® F 87 EO/PO/EO triblock copolymers. PLURONIC® P 85 is 4–9% by weight of the cleansing composition, PLURONIC® F 87 is 0.5–2% by weight of the cleansing composition. U.S. Pat. No. 5,096,698 discloses a dental creme composition containing a non-ionic triblock liquid EO/PO/EO copolymer or a solid triblock EO/PO/EO copolymer at levels of 0.1–5% by weight. Said copolymers help to prevent phase separation. PLURONIC® F 108 (solid) is most preferred, followed by PLURONIC® F 87, PLURONIC® F 127, and PLURONIC® L 72. Liquid and solid PLURONIC® surfactants are not used together in said dental creme composition. Finally, U.S. Pat. No. 5,709,852 discloses a nonaqueous carrier for personal care compositions comprising: (a) nonionic liquid triblock EO/PO/EO copolymer and (b) nonionic solid triblock EO/PO/EO copolymer.

However, the art does not disclose a blend of a liquid polyoxyalkylene compound and a solid ethylene oxide/propylene oxide/ethylene oxide (EO/PO/EO) triblock copolymers, as stable non-aqueous carrier blends for personal care compositions. Applicants have surprisingly discovered that blends of a liquid polyoxyalkylene compound and solid EO/PO/EO triblock copolymers significantly improve the rheological consistency, maintain freeze/thaw stability and provide adequate thermal stability for personal care products.

SUMMARY

A stable, non-aqueous carrier for personal care compositions comprising:
a) about 80–98% by weight of a liquid polyoxyalkylene compound of molecular weight (MW) 1000–100,000;
b) about 2–20% by weight of a non-ionic solid triblock EO/PO/EO copolymer of molecular weight (MW) 8500–25,000

DETAILED DESCRIPTION

A stable, non-aqueous carrier for personal care compositions comprising:
a) about 80–98% by weight of a liquid polyoxyalkylene compound of molecular weight (MW) 1000–100,000;
b) about 2–20% by weight of a non-ionic, solid triblock EO/PO/EO copolymer of molecular weight (MW) 8500–25,000

The Non-Ionic Solid Triblock EO/PO/EO Copolymer of MW 6000–25000

The non-ionic, solid, triblock EO/PO/EO copolymers of molecular weight 8500–25000, of the present invention, are represented by the formula:

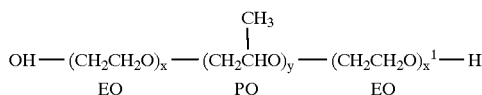
EO     PO     EO herein x and $x^1$ and y are integers not equal to zero; x and $x^1$ represent the umber of EO units in said solid triblock copolymer; y represents the number of PO units in said solid triblock copolymer.

Preferably, the molecular weight (MW) is 8,500 to 25,000; more preferably, the molecular weight is 9500–16,000; most preferably, the molecular weight is 10,000–15,000.

Preferred nonionic, solid EO/PO/EO triblock copolymers useful in the practice of the present invention are:

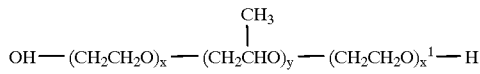

wherein $x+x^1=194$; $y=39$; molecular weight=10800.
More preferred nonionic, solid EO/PO/EO triblock copolymers are:

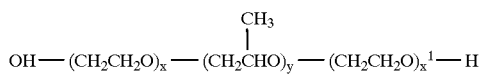

wherein $x+x^1=244$; $y=47$; molecular weight=13500.
Most preferred nonionic, solid EO/PO/EO triblock copolymers are:

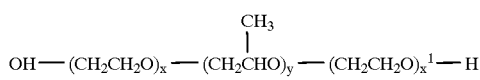

wherein $x+x^1=256$; $y=54$; molecular weight=14000; and

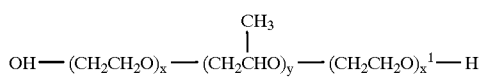

wherein $x+x^1=196$; $y=58$; molecular weight=11500.

The Liquid Polyoxyalkylene Compound of MW 1000 –100,000

The liquid polyoxyalkylene compound of MW 1000–100000 are represented by the formula:

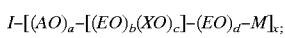

wherein
I is a initiator or a mixture of initiators having at least one substituent selected from the group including, but not limited to, OH, NH2, or COOH;
AO is an alkylene oxide having 2–6 carbon atoms or a mixture of alkylene oxides having 2–6 carbon atoms;
EO is ethylene oxide;
XO is an alkylene oxide moiety having 3–6 carbon atoms;
M is hydrogen or alkali or an alkaline earth metal;
a is an integer from about 0–20;
b is an integer from about 5–1500;
c is an integer from about 1–400;
d is an integer from about 0–15;
x is an integer from about 1–8;
Further, the amount of alkylene oxide, (XO) and (AO), in the molecule will never exceed 25% of the molecular weight of the liquid polyoxyalkylene compound.
Further, AO, EO, and XO are arranged randomly.
Preferably, the molecular weight =1000–100,000; more preferably, the molecular weight=1500–15,000; most preferably, the molecular weight 2000–5000.
Preferred liquid polyoxyalkylene compounds useful in the practice of the present invention are:

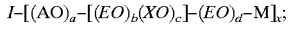

wherein I=propylene glycol; a and d=0; XO is propylene oxide, b is from 10–500, c is from 1–250, x is 2, and the molecular weight is from about 1000–75000.

More preferred liquid polyoxyalkylene compounds are:

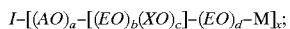

wherein I=propylene glycol; a and d=0; XO is propylene oxide, b is from 5–250, c is from 1–125, x is 2 and the molecular weight from about 1000–36600

Most preferred liquid polyoxyalkylene compounds are:

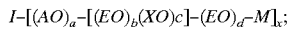

wherein I=propylene glycol, AO is ethylene oxide or a mixture of ethylene oxide and propylene oxide, XO is propylene oxide, M is hydrogen, a is 28, b is 7–16, c is 1–10, d is 1–5, and x is 2.

Said liquid polyoxyalkylene compounds include only random copolymers of alkylene oxides, and excludes liquid, block copolymers of ethylene oxide and propylene oxide or liquid polyethylene glycols.

Preparation of the Stable Non-Aqueous Carrier Blends of the Present Invention The stable, non-aqueous carrier blends useful in personal care compositions are prepared by blending the liquid polyoxyalkylene compound with the solid nonionic triblock EO/PO/EO copolymer. Preferably, 80–98% by weight of the liquid polyoxyalkylene compound is blended with 2–20% by weight of the solid nonionic triblock copolymer. More preferably, 85–95% by weight of the liquid polyoxyalkylene compound is blended with 5–15% by weight of the solid nonionic triblock copolymer. Most preferably, 88–92% of the liquid polyoxyalkylene compound is blended with 8–12% of the solid nonionic triblock copolymer.

The resulting composition is then heated to about 70° C. or until a clear, single-phase composition is obtained. The composition is then cooled with stirring on a Lightnin® mixer set at 100 rpm until the temperature of the composition is ambient (~35° C). The composition is then allowed to equilibrate for 24 hours at room temperature (~25C). At the end of the equilibration period, the composition is opaque is appearance and has the consistency of a ointment paste.The viscosity of the composition was determined using a Brookfield Cone/Plate rotational viscometer. A portion of the composition was stored in an oven mantained at 50° C. for a period of thirty days. At the end of the thirty day period, observations were made regarding the stability of the composition. Stability of the composition refers to its physical stability, i.e whether the composition splits in to two phases or remains a opaque, single phase composition. The composition is then allowed to cool to ambient temperature and allowed to equilibrate to room temperature for a period of 24 hours. At the end of the equilibration period, the Brookfield viscosity of the composition is determined.

Preparation of Personal Care Compositions Containing the Stable Non-Aaueous Carrier Blends of the Present Invention Personal care compositions comprising these stable non-aqueous carrier blends, prepared as described hereinabove, preferably contain 10–90% by weight of the stable non-aqueous carrier blends of the present invention; more preferably 2585%; most preferably, 40–80% by weight of the said carrier blend in the personal care formulation in which said stable carrier is used.

Personal care formulations comprising these stable non-aqueous carrier blends may further contain other ingredients such as surfactants selected from anionic surfactants, such as sodium lauryl sulphate; sodium alkyl glyceryl ether sulfonate; alkyl benzene sulfonates. Further, small amounts of cationic surfactants having a quaternary nitrogen, which show compatibility with the nonionic carrier blends of this invention can also be used. Various other materials may also be used in the formulating of personal care products. For example, in a dentrifice, dental abrasives consisting of finely divided silica, or calcium carbonate, calcium pyrophosphate, and hydrated alumina are added for polishing performance. Additionally, thickening agents such as xanthan gum, gum arabic, hydroxyethylcellulose can also be used to provide sufficient thickening consistency to the formulation. Also, flavoring agents such as peppermint, spearmint oils or preservatives, opacifying agents, buffer salts, sweeteners, anti-bacterial agents or anti-plaque agents, anti-inflammatory agents, anti-caries agents such as the fluoride salts can also be included in small amounts. Polymeric agents which accelerate the transport of active materials can also be included. Also, in cosmetic creams emollients such as glycerin, mineral oil and petrolatum can be added.

Personal care products are formulated according to methods known to those skilled in the art. Representative personal care product formulations are disclosed in: *Cosmetics, Science and Technology*, 2nd Edition, Vol. 1, Edited by M. S. Balsam, et al., and *A Formulary of Cosmetic Preparations*, Michael and Irene Ash, Chemical Publishing, N.Y., N.Y., both incorporated by reference herein.

The following non-limiting Examples serve to illustrate the utility of the present invention. All percentages are weight percent (%) of the total composition unless otherwise indicated.

Dentrifice Composition 10 to 55% abrasive, selected from the group including, but not limited to, anhydrous dicalcium phosphate, calcium carbonate, calcium pyrophosphate.

0.2 to 0.8% stannous fluoride, sodium monofluorophosphate 2 to 10% binders, including, but not limited to, gum karaya, tragacanth USP, sodium alginate; Irish moss and methyl cellulose.

2 to 8% surfactants, including, but not limited to, sodium lauryl sulfate, sodium-N-lauryl sarcosinate; dioctyl sodium sulfosuccinate.

10 to 50% humectants, including, but not limited to, glycerin; propylene glycol; sorbitol; polyethylene glycol.

25 to 85% non-aqueous carrier blend of the present invention comprising:
  i) about 80–98% by weight of a liquid polyoxylalkylene compound of MW 3000–100,000;
  ii) about 2–20% by weight of a non-ionic solid triblock EOIPO/EO copolymer of MW 8500–25,000.

Body Wash Composition 1 to 5% emollients, including, but not limited to, lanolin, sterols (cholesterol) and fatty acids.

0.1 to 3% barrier agents, including but not limited to, petrolatum, beeswax; casein.

0.01 to 0.1% healing agents, including, but not limited to, allantoin and urea.

2 to 20% humectants, including, but not limited to, glycerin; propylene glycol; sorbitol; polyethylene glycol.

0.01 to 1% thickeners, including but not limited to, guar gum, cellulose derivatives and Irish moss.

0.5 to 3% emulsifiers, including but not limited to, cetyl pyridimium chloride; polyoxyethylene lauryl alcohol.

25 to 85% non-aqueous carrier blend comprising:
 i) about 80–98% by weight of a liquid polyoxyalkylene compound of MW 3000–100,000;
 ii) about 2–20% by weight of a non-ionic, solid triblock copolymer of MW 8500–25,000.

Hydrocortisone Ointment Composition 1 to 5% hydrocortisone 2 to 20% petrolatum 25 to 85% non aqueous carrier blend comprising:
 i) about 80–98% by weight of a liquid, polyoxyalkylene compound of MW 3000–100000;
 ii) about 2–20% by weight of a non-ionic solid triblock EO/PO/EO copolymer of MW 8500–25,000.

We claim:

1. A stable non aqueous carrier for personal care compositions comprising:
 a) about 80–98% by weight of a liquid polyoxyalkylene compound having the formula:

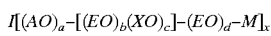

wherein I=propylene glycol, a and d=O, XO=propylene glycol, b is from 10–500; c is from 1–250; X=2, and the molecular weight is from 1,000 to 25,000;
 b) about 2–20% by weight of a non-ionic solid triblock EO/PO/EO copolymer having the formula:

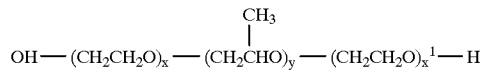

wherein $x+x^1=194$; $y=39$; the molecular weight is 10,800.

2. A stable non aqueous carrier for personal care compositions comprising:
 a) about 80–98% by weight of a liquid polyoxyalkylene compound having the formula:

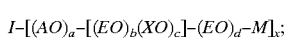

wherein I=propylene glycol; a and d=0; XO is propylene oxide, b is from 5–250, c is from 1–125, x is 2 and the molecular weight from about 1000–36600;
 b) about 2–20% by weight of a non-ionic solid triblock EO/PO/EO copolymer having the formula:

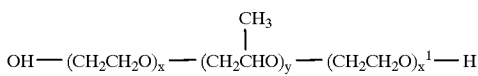

wherein $x+x^1=244$; $y=47$; molecular weight=13500.

3. A stable non aqueous carrier for personal care compositions comprising:
 a) about 80–98% by weight of a liquid polyoxyalkylene compound having the formula:

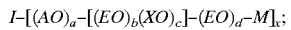

wherein I=propylene glycol, AO is ethylene oxide or a mixture of ethylene oxide and propylene oxide, XO is propylene oxide, M is hydrogen, a is 2–8, b is 7–16, c is 1–10, d is 1–5, and x is 2;
 b) about 2–20% by weight of a non-ionic solid triblock EO/PO/EO copolymer having the formula:

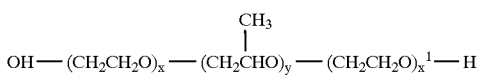

wherein $x+x^1=256$; $y=54$; molecular weight=14000.

4. A stable non aqueous carrier for personal care compositions comprising:
 a) about 80–98% by weight of a liquid polyoxyalkylene compound having the formula:

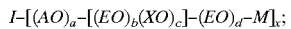

wherein I=propylene glycol, AO is ethylene oxide or a mixture of ethylene oxide and propylene oxide, XO is propylene oxide, M is hydrogen, a is 2–8, b is 7–16, c is 1–10, d is 1–5, and x is 2;
 b) about 2–20% by weight of a non-ionic solid triblock EO/PO/EO copolymer having the formula:

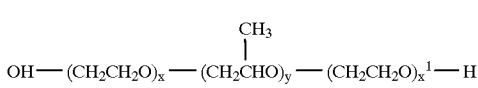

wherein $x+x^1=196$; $y=58$; molecular weight=11500.

* * * * *